United States Patent [19]

Suganuma et al.

[11] Patent Number: 4,581,228

[45] Date of Patent: * Apr. 8, 1986

[54] TOOTHPASTE COMPOSITION AND PLASTIC CONTAINERS CONTAINING THE SAME

[75] Inventors: Nobuo Suganuma, Funabashi; Kensuke Tanaka, Kashiwa; Nobuyuki Takada, Chigasaki; Hiromichi Ichikawa, Matsudo, all of Japan

[73] Assignee: Lion Corporation, Tokyo, Japan

[ * ] Notice: The portion of the term of this patent subsequent to Dec. 3, 2002 has been disclaimed.

[21] Appl. No.: 316,400

[22] Filed: Oct. 29, 1981

[30] Foreign Application Priority Data

Nov. 20, 1980 [JP]  Japan .............................. 55-163739

[51] Int. Cl.$^4$ .......................... A61K 7/16; A61K 7/18
[52] U.S. Cl. ........................................ 424/52; 424/49; 206/277; 206/524.1; 206/524.3; 222/107
[58] Field of Search ................... 206/277, 524.1, 524.3; 222/107; 424/49, 58, 52

[56] References Cited

U.S. PATENT DOCUMENTS

| | | | |
|---|---|---|---|
| 2,010,910 | 8/1935 | Atkins | 424/49 |
| 2,136,033 | 11/1938 | Van Rossem | 206/524.3 |
| 2,550,207 | 4/1951 | Tainter et al. | 424/49 |
| 2,671,995 | 3/1954 | Egan | 206/524.3 |
| 2,671,996 | 3/1954 | Schneider | 206/524.3 |
| 2,818,371 | 12/1957 | Wessinger | 424/52 |
| 2,984,570 | 5/1961 | Prell | 206/277 |
| 3,060,098 | 10/1962 | Gershon | 424/52 |
| 3,115,248 | 12/1963 | Sellinger et al. | 206/524.3 |
| 3,160,323 | 12/1964 | Weisberg | 206/277 |
| 3,182,795 | 5/1965 | Pryor | 206/524.3 |
| 3,295,725 | 1/1967 | Brandt | 222/107 |
| 3,313,455 | 4/1967 | Kemmer | 206/277 |
| 3,342,330 | 9/1967 | Buchanan | 206/524.3 |
| 3,505,143 | 4/1970 | Haas et al. | 222/107 |
| 3,565,293 | 2/1971 | Schultz | 222/107 |
| 3,599,837 | 8/1971 | Anderson | 222/107 |
| 3,622,661 | 11/1971 | King et al. | 424/50 |
| 3,958,721 | 5/1976 | Kushida et al. | 222/107 |
| 4,011,968 | 3/1977 | McGhie et al. | 222/107 |
| 4,098,878 | 7/1978 | Baines et al. | 424/52 |
| 4,118,471 | 10/1978 | Pensak | 424/52 |
| 4,123,517 | 10/1978 | Baines et al. | 424/49 X |
| 4,142,630 | 3/1979 | Hayes et al. | 206/277 |
| 4,150,113 | 4/1979 | Hoogendoorn et al. | 424/50 |
| 4,168,301 | 9/1979 | Pugh et al. | 424/49 |
| 4,196,825 | 4/1980 | Kincaid | 222/107 |
| 4,265,948 | 5/1981 | Hayes et al. | 206/277 |
| 4,269,822 | 5/1981 | Pellico et al. | 424/50 |

FOREIGN PATENT DOCUMENTS

| | | | |
|---|---|---|---|
| 1948469 | 4/1971 | Fed. Rep. of Germany | 424/50 |
| 52-54037 | 5/1977 | Japan | 424/50 |
| 1197164 | 7/1970 | United Kingdom | 424/50 |
| 1272454 | 4/1972 | United Kingdom . | |
| 1373003 | 11/1974 | United Kingdom | 424/50 |

OTHER PUBLICATIONS

Hercules, "Cellulose Gum", pp. 1–5.
Daicel Ltd., Product Information.

*Primary Examiner*—Shep K. Rose
*Attorney, Agent, or Firm*—Birch, Stewart, Kolasch & Birch

[57] ABSTRACT

A plastic container is filled with an antiseptic toothpaste composition comprising an aluminum oxide compound such as aluminum oxide trihydrate as a main abrasive and a polyhydric alcohol such as propylene glycol, sorbitol, etc. in an amount of 5 to 100 moles in fluoride-free systems or 4.0 to 100 moles in fluoride-containing systems per liter of water in the toothpaste composition.

21 Claims, 1 Drawing Figure

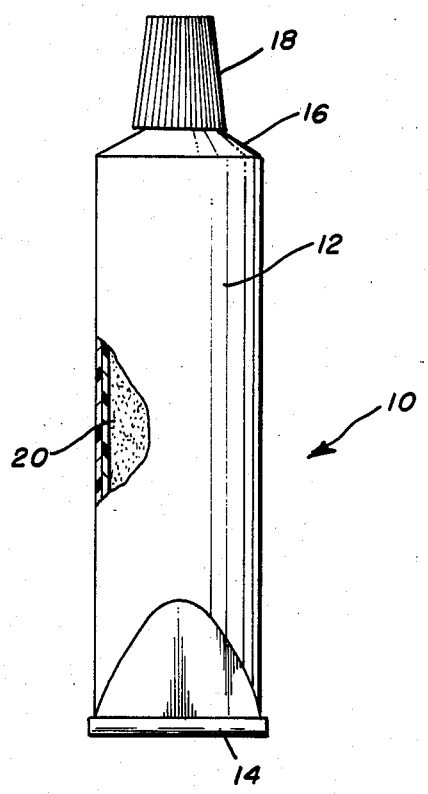

TOOTHPASTE COMPOSITION AND PLASTIC CONTAINERS CONTAINING THE SAME

BACKGROUND OF THE INVENTION

This invention relates to toothpaste compositions with which plastics containers are filled. More particularly, this invention relates to toothpaste compositions which exhibit increased antiseptic properties when received in plastics containers including plastics tubes, aluminum foil-plastics coating laminate tubes and plastics bottles.

In general, toothpaste compositions are contained in suitable containers and squeezed out of the containers onto a toothbrush immediately before they are used. It is therefore required that such toothpaste is kept hygienically acceptable in the container, easily extruded through a container opening, easily applied onto a tooth brush, and retains its shape on the toothbrush.

Commonly used toothpaste containers are generally classified into two groups; metal containers including aluminium tubes and plastic containers including plastics tubes formed solely of plastics material, laminate tubes comprising an aluminium foil coated with a plastics layer on an inner or each surface and formed into a tube, and plastic bottles. Such a plastics bottle has a wall of substantial thickness and can restore its shape immediately after the pressure applied to squeeze a desired amount of toothpaste out of the bottle is released. The plastics bottle has an aesthetic appearance and can stand on its cap, requiring a minimum space.

Among these containers, as a result of the interaction of a container with its contents or toothpaste composition, metal containers, especially aluminum tubes are susceptible to corrosion or pitting. This problem may be overcome by modifying the formulation of toothpaste compositions or by replacing aluminum tubes by plastics containers.

Concerning plastics containers, no substantial problem has heretofore been found when toothpaste compositions are received in plastics containers including plastic tubes, plastics bottles, and laminate tubes comprising an aluminum foil coated with a plastics layer on an inner or each surface. However, the inventors have experimentally discovered that if contaminants are accidentally introduced into a toothpaste container from the environment, plastics containers capable of more or less restoring their shape immediately after the pressure applied to squeeze a desired amount of toothpaste out of the container is released allow aerobic bacteria to grow or propagate easily in their contents or toothpaste as compared with aluminum tubes. Although aerobic bacteria are not pathogenic, the presence of such bacteria in a substantial quantity would have undesired influence on the flavor and stability of toothpaste compositions. It has been thus found that toothpaste compositions should be more antiseptic when plastic containers, particularly those containers with a high restoring force are used.

In general, conventional toothpastes are rendered antiseptic by incorporating antiseptics and bactericides therein. However, some bactericides, for example, quarternary ammonium salt bactericides have been reported as coloring tooth enamel. In addition, the use of such antiseptics and bactericides is strictly limited by Governmental regulations. Since toothpaste compositions are destined for oral application, it is desired for increased hygienic safety that the amount of antiseptics and bactericides blended is as small as possible.

SUMMARY OF THE INVENTION

It is, therefore, an object of the present invention to provide an improved toothpaste composition which exhibits increased antiseptic properties with a minimum amount of an antiseptic and/or bactericide when filled in a plastics container.

Toothpaste compositions to which the present invention is directed are to be received in plastics containers including plastics bottles, plastics tubes and aluminum foil-plastic coating laminate tubes. According to the present invention, the toothpaste composition comprises an aluminum oxide compound as a main abrasive and a polyhydric alcohol. The polyhydric alcohol is blended in an amount of 5.0 to 100 moles per liter of water in the toothpaste composition when the composition is free of any fluoride. The polyhydric alcohol is blended in an amount of 4.0 to 100 moles per liter of water in the toothpaste composition when the composition contains a fluoride.

The toothpaste compositions of the present invention which contain an aluminum oxide compound as a main abrasive and a polyhydric alcohol in an amount of 5.0 to 100 moles in fluoride-free systems or 4.0 to 100 moles in fluoride-containing systems per liter of water in the toothpaste compositions have high antiseptic power against aerobic bacteria. The use of a polyhydric alcohol in the above-defined contents in combination with an aluminum oxide abrasive renders the toothpaste compositions highly antiseptic. Even when the toothpaste compositions are accidentally contaminated with a substantial amount of bacteria, such contamination will be diminished within a relatively short period of time. Since the toothpaste compositions of the present invention are effective to suppress the growth of aerobic bacteria, they may be advantageously stored in plastics containers having a high restoring force for a long period of time without a change in quality. According to the present invention, an antiseptic and/or bactericide may be blended in a minimum amount so that the toothpaste compositions of the present invention are highly safe for oral application.

The above and other objects, features and advantages of this invention will become more apparent and understandable from the following Detailed Description, Examples and Claims.

BRIEF DESCRIPTION OF THE DRAWING

The sole Figure of the Drawing is a partially broken away side view of a plastic toothpaste container filled with the composition of the present invention.

DETAILED DESCRIPTION OF THE INVENTION

The toothpaste composition of this invention comprises an aluminium oxide compound as a main abrasive and a polyhydric alcohol.

The aluminum oxide compounds represented by the general formula:

$$Al_2O_3 \cdot nH_2O \qquad (1)$$

wherein $n \geq 0$, preferably $3 \geq n \geq 0$, include aluminum oxide when $n=0$ (that is, an aluminum compound having no water of crystallization and represented by $Al_2O_3$, to be referred to as "alumina", hereinafter) and hydrated aluminum oxides when $n>0$ (that is, aluminum compounds having water of crystallization, to be referred to as "hydrated aluminas", hereinafter).

Many types of aluminas and hydrated aluminas are known including α, γ, δ, η, θ, κ, χ, ρ and β types classified in terms of crystal systems and physical properties. Among them, α-alumina and hydrated α-alumina are preferred because of high stability.

The hydrated aluminas which can be used herein are gibbsite and bayerite (represented by $Al_2O_3.3H_2O$, respectively), boehmite and diaspore (represented by $Al_2O_3.H_2O$, respectively) and the like.

Among these aluminum oxide compounds, hydrated aluminas are preferred in view of abrasiveness, tooth abrasion and the like. Alumina trihydrates having the formula:

$$Al_2O_3.3H_2O \text{ or } Al(OH)_3 \qquad (2)$$

are most preferred because of their mild abrasiveness. The preferred alumina trihydrate is gibbsite which is commercially available.

The aluminum oxide compounds may be used alone or in admixture of two or more.

In view of tooth cleaning and abrasing effects, the aluminum oxide compound should be in the form of particles having an average particle size of 1–50 microns, preferably 3–25 microns when measured by the sedimentation method. The aluminum oxide compound is blended in an amount of 10 to 70% by weight, preferably 30 to 60% by weight of the total weight of the toothpaste composition although the exact blending amount may vary with a particular type of the toothpaste composition.

In addition to the aluminum oxide compound incorporated as the main abrasive as mentioned above, the toothpaste composition of this invention may further include other additional abrasives, for example, dicalcium phosphate dihydrate and anhydride, calcium carbonate, calcium pyrophosphate, silica, aluminum silicate, insoluble sodium metaphosphate, magnesium tertiary phosphate, magnesium carbonate, synthetic resins and other known abrasives alone or in admixture generally in an amount of less than about 10% by weight in terms of the weight of the aluminium oxide compound.

The polyhydric alcohols which can be used in the present invention include ethylene glycol, propylene glycol, 1,3-butylene glycol, polyethylene glycol, glycerine, sorbitol, xylitol, maltitol, lactitol, etc. and mixtures thereof.

Amounts of the polyhydric alcohols blended fall within the range of 5.0 to 100 moles in fluoride-free systems or within the range of 4.0 to 100 moles in fluoride-containing systems per liter of water in the toothpaste compositions. The presence of polyhydric alcohols in the above-defined ranges is effective to preclude aerobic bacteria from growing or propagating in plastics containers, providing highly antiseptic toothpaste compositions.

In general, the higher the molar number of a polyhydric alcohol, the more effective it is. However, the upper limit of the molar number of a polyhydric alcohol is 100 moles, preferably 50 moles for reasons of toothpaste feeling and cost. More strictly, the upper limit is 15 moles when the smoothness and stringiness of toothpaste upon extrusion are taken into account.

According to the present invention, a fluoride may preferably be blended in the toothpaste composition in addition to the polyhydric alcohol. The fluoride is effective to further improve the antiseptic properties of the toothpaste composition and to lower the lower limit of the amount of the polyhydric alcohols blended as understood from the above-defined ranges. Examples of the fluorides are stannous fluoride, sodium fluoride, and alkali metal monofluorophosphates such as sodium monofluorophosphate, and potassium monofluorophosphate, with the monofluorophosphates being preferred. The fluoride compounds such as alkali metal monofluorophosphates, when blended in an amount of 0.1 to 1% by weight of the total weight of the toothpaste composition, ensure satisfactory antiseptic action and tooth enamel reinforcement.

Preferably, the toothpaste composition of the present invention may further contain as a binder an alkali metal salt of carboxymethyl cellulose such as sodium carboxymethyl cellulose because of the effectiveness to enhance the antiseptic properties of the toothpaste composition. The alkali metal salts of carboxymethyl cellulose may preferably be those having an average degree of etherification of 0.75 to 0.90 because these salts are effective for shape retention of the toothpaste composition. With degrees of etherification of lower than 0.75, the toothpaste compositions become too hard so that an extrudate of toothpaste will readily tumble down from a toothbrush when applied onto the toothbrush. On the other hand, if the average degree of etherification exceeds 0.90, the shape retention of toothpaste becomes lower with repeated squeezing of a plastics container than in the case of an aluminum tube so that an extrudate of toothpaste will undesirably flow on a toothbrush. The carboxymethyl cellulose salts may preferably be blended in an amount of 0.2 to 5%, particularly 0.5 to 2% by weight of the total weight of the toothpaste composition.

The toothpaste composition of the present invention may further contain other additives well known in the art. Examples of such additives include anionic and nonionic surface active agents. The anionic surface active agents may include water-soluble salts of the higher alkyl sulfates having 8 to 18 carbon atoms in the alkyl group (e.g., sodium lauryl sulfate and sodium mirystyl sulfate), water-soluble salts of sulfonated monoglycerides of higher fatty acids having 10 to 18 carbon atoms in the fatty acid group (e.g. sodium lauryl monoglyceride sulfonate and sodium coconut monoglyceride sulfonate), salts of amides of higher fatty acid having 12 to 16 carbon atoms in the fatty acid group with lower aliphatic amino acids (e.g. sodium-N-methyl-N-palmitoyl touride, sodium N-lauroyl sarcosinate, sodium N-methyl glutamate and sodium N-lauroyl-β-alanine), etc. The nonionic surface active agents may include alkyrol diethanol amides (e.g. lauroyl diethanol amide), stearyl monoglyceride, sucrose fatty acid esters having 12 to 18 carbon atoms in the fatty acid group (e.g. sucrose monolaurate and dilaurate), lactose fatty acid esters, lactitol fatty acid esters, maltitol fatty acid esters, condensates of sorbitan monostearate with approximately 60 moles of ethylene oxide, condensates of ethylene oxide with propylene oxide condensates of propylene glycol and their derivatives (e.g. polyoxyethylene polyoxypropylene monolauryl ester), etc. The toothpaste composition may also contain amphoteric surface active agents such as those of betaine and amino acid types, etc. These surface active agents may be blended alone or in admixture in an amount of 0.2 to 7% by weight of the composition.

Also included are flavors such as spearmint oil and peppermint oil (in an amount of 0.1 to 3% by weight), clove oil, cassia oil, sage oil, coriander oil, anise oil, wintergreen oil, eucalyptus oil, and fruit flavors (in an amount of 0.001 to 1% by weight). Such a natural essential oil may be partially replaced by a synthetic or isolated flavor, for example, l-menthol, anethole, carvone, eugenol, etc. Furthermore, sweeteners such as sodium saccharin, stevioside, neohesperidin dihydrocalcone, glycyrrhizin, perillartine, p-methoxycinnamic aldehyde, etc. may be blended.

The toothpaste composition of the present invention may contain humectants other than polyhydric alcohols as well as binders other than alkali metal salts of carboxymethyl cellulose. Examples of the other binders include carrageenan, alkali metal alginates such as sodium alginate, gums such as xanthan gum, synthetic binding agents such as polyvinyl alcohol, inorganic binding agents such as silica gel, veegum, aluminum silicate gel, etc. and mixtures thereof. The other binders may be blended alone or in admixture, preferably in admixture with alkali metal salts of carboxymethyl cellulose in an amount of 0 to 2% by weight of the composition.

In addition to fluorides, the toothpaste composition of this invention may further include other active ingredients, for example, enzymes such as dextranase, amylase, protease, mutanase, lysozyme, lytic enzyme, etc., stannous compounds, $\epsilon$-aminocaproic acid, tranexamic acid, aluminum chlorohydroxyallantoinate, dihydrocholesterol, glycyrrhetinates, glycerophosphate, sodium chloride, water-soluble inorganic phosphates, and the like alone or in admixture. Examples of the water-soluble inorganic phosphate are potassium and sodium salts of orthophosphoric acid, pyrophosphoric acid and polyphosphoric acid, while the potassium salts are preferred.

In the toothpaste composition, antiseptics such as ethyl p-hydroxybenzoate and butyl p-hydroxybenzoate, and bactericides such as bactericidal quarternary ammonium salts and chlorhexidine and its salts may be blended in an amount of 0 to 0.5% by weight of the composition.

Other well-known ingredients may also be blended in the composition.

The toothpaste composition of the present invention may be prepared by selecting the necessary ingredients from the above-mentioned ingredients and kneading them with water.

The toothpaste composition according to this invention may generally have a pH of 4.5 to 10, preferably 6 to 8.5.

As shown in the drawing, the thus prepared toothpaste composition 20 is packed into a plastics container such as a collapsable plastic tube 10 having a tubular body 12 and a cap 18. The plastics tube may be The thus prepared toothpaste composition is packed into a plastic container including a plastic tube formed solely of plastics material, an aluminum foil-plastics coating laminate tube which comprises an aluminium foil coated with a plastics layer on an inner or each surface and formed into a tube, and a plastic bottle. Plastic material of the plastic containers may be selected from ethylene-vinyl alcohol copolymer, polyvinylidene chloride, polyvinyl chloride, nylon, polyester, polyethylene, polypropylene, etc. The toothpaste composition of the present invention may be advantageously and safely stored in the plastics container for a long period of time without a change in quality because they are effective to prevent aerobic bacteria from growing or propagating.

The following examples are illustrative of this invention. However, it is to be understood that the invention is not limited to the examples. All percents are by weight.

EXAMPLE 1

Twelve toothpaste compositions each having the formulation shown in Table 1 were prepared in a conventional manner.

TABLE 1

| Ingredients (% by weight) | SAMPLE NO. | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Dicalcium phosphate dihydrate | 52.0% | 49.6% | 46.9% | | | | 52.0% | 49.6% | 46.9% | | | |
| Alumina trihydrate (gibbsite, average particle size 9 microns) | | | | 52.0% | 49.6% | 46.9% | | | | 52.0% | 49.6% | 46.9% |
| Propylene glycol | 2.5 | 2.5 | 2.5 | 2.5 | 2.5 | 2.5 | 2.5 | 2.5 | 2.5 | 2.5 | 2.5 | 2.5 |
| Sorbitol | 15.0 | 18.0 | 21.0 | 15.0 | 18.0 | 21.0 | 12.0 | 15.0 | 18.0 | 12.0 | 15.0 | 18.0 |
| Sodium carboxymethyl cellulose (average etherification degree 0.78) | 0.6 | 0.6 | 0.6 | 0.6 | 0.6 | 0.6 | 0.6 | 0.6 | 0.6 | 0.6 | 0.6 | 0.6 |
| Carrageenan | 0.4 | 0.4 | 0.4 | 0.4 | 0.4 | 0.4 | 0.4 | 0.4 | 0.4 | 0.4 | 0.4 | 0.4 |
| Sodium saccharin | 0.15 | 0.15 | 0.15 | 0.15 | 0.15 | 0.15 | 0.15 | 0.15 | 0.15 | 0.15 | 0.15 | 0.15 |
| Sodium lauryl sulfate | 1.5 | 1.5 | 1.5 | 1.5 | 1.5 | 1.5 | 1.5 | 1.5 | 1.5 | 1.5 | 1.5 | 1.5 |
| Flavor | 1.0 | 1.0 | 1.0 | 1.0 | 1.0 | 1.0 | 1.0 | 1.0 | 1.0 | 1.0 | 1.0 | 1.0 |
| Sodium monofluorophosphate | 0 | 0 | 0 | 0 | 0 | 0 | 0.76 | 0.76 | 0.76 | 0.76 | 0.76 | 0.76 |
| Water | 26.85 | 26.25 | 25.95 | 26.85 | 26.25 | 25.95 | 29.09 | 28.49 | 28.19 | 29.09 | 28.49 | 28.19 |
| Total | 100.0 | 100.0 | 100.0 | 100.0 | 100.0 | 100.0 | 100.0 | 100.0 | 100.0 | 100.0 | 100.0 | 100.0 |
| Total mole number of polyhydric alcohols (mol/l of water) | 4.3 | 5.0 | 5.7 | 4.3 | 5.0 | 5.7 | 3.4 | 4.0 | 4.7 | 3.4 | 4.0 | 4.7 |

In Table 1, sample Nos. 5, 6, 11 and 12 fall within the scope of the present invention and other samples are shown for the purpose of comparison These samples were tested for antiseptic properties by the following method.

Gram-negative bacillus was isolated from the environment and stored in a slant. A trypticase soy plateoculture medium was smeared with the bacillus. After cultivation at 32° C. for 48 hours, the bacillus which had grown on the plate was scraped and suspended in a sterilized physiological saline solution to form a thick bacillus suspension.

The toothpaste samples were inoculated with the above-prepared bacillus suspension to a concentration of $10^6$–$10^7$ bacillus/g of toothpaste and thoroughly kneaded. Laminate tubes formed of an aluminum foil coated with a polyethylene film on each surface were filled with the contaminated toothpaste samples and stored at 30° C. The number of surviving bacilli in the toothpaste samples was determined after 1, 2 and 4 weeks. The results are shown in Table 2.

The evaluation standard is as follows.

TABLE 2

| Sample No. | Molar number of polyhydric alcohol | Abrasive | Sodium mono-fluorophosphate | Number of surviving bacilli Storage period | | |
|---|---|---|---|---|---|---|
| | | | | 1 week | 2 weeks | 1 month |
| 1 | 4.3 | Dicalsium phosphate | 0 | ++ | ++ | ++ |
| 2 | 5.0 | " | 0 | ++ | ++ | ++ |
| 3 | 5.7 | " | 0 | ++ | ++ | ++ |
| 4 | 4.3 | Alumina trihydrate | 0 | ++ | ++ | ++ |
| 5 | 5.0 | " | 0 | ± | — | — |
| 6 | 5.7 | " | 0 | — | — | — |
| 7 | 3.4 | Dicalcium phosphate | 0.76% | ++ | ++ | ++ |
| 8 | 4.0 | " | 0.76% | ++ | ++ | ++ |
| 9 | 4.7 | " | 0.76% | ++ | ++ | ++ |
| 10 | 3.4 | Alumina trihydrate | 0.76% | ++ | ++ | ++ |
| 11 | 4.0 | " | 0.76% | ± | — | — |
| 12 | 4.7 | " | 0.76% | — | — | — |

++: $\geq 10^5$/g
+: $10^3$–$10^5$/g
±: about $10^2$/g
—: $\leq 10$/g

As seen from the data of Table 2, satisfactorily antiseptic toothpaste compositions are obtained using alumina abrasive in combination with at least 5.0 moles of a polyhydric alcohol in fluoride-free systems or at least 4.0 moles of a polyhydric alcohol in fluoride-containing systems.

Aluminum tubes and laminate tubes formed of an aluminum foil having a polyethylene coating on each surface were filled with toothpaste sample Nos. 1 to 6. After being stored at room temperature and 50° C. for one month, the samples were measured for stability. All the toothpaste samples themselves were found to be satisfactorily stable. However, corrosion and blister were observed in those aluminum tubes filled with toothpaste sample Nos. 4 to 6 containing alumina trihydrate abrasive. No problem occurred in the laminate tubes filled with the same samples. Neither the aluminum tubes nor the laminate tubes gave rise to any problem when they were filled with toothpaste sample Nos. 1 to 3 containing dicalcium phosphate abrasive.

EXAMPLE 2

| | % by weight |
|---|---|
| Alumina trihydrate ($Al_2O_3 \cdot 3H_2O$, gibbsite, average particle size 10μ) | 45 |
| Glycerine | 15 ⎫ |
| Sorbitol | 10 ⎬ (8.3 moles/l) |
| Sodium carboxymethyl cellulose (average degree of etherification 0.85) | 1.0 ⎭ |
| Sodium saccharin | 0.1 |
| Sodium lauryl sulfate | 1.5 |
| Flavor (peppermint type) | 1.0 |
| Water | 26.4 |
| | 100.0% |

A plastics tube was filled with the above composition.

EXAMPLE 3

| | % by weight | |
|---|---|---|
| Alumina trihydrate ($Al_2O_3 \cdot 3H_2O$, average particle size 15μ) | 27 | |
| Silica | 3 | |
| Sorbitol | 33 | (5.5 moles/l) |
| Sodium carboxymethyl cellulose (average degree of etherification 0.77) | 0.5 | |
| Carrageenan | 0.5 | |
| Sodium saccharin | 0.1 | |
| Sodium lauryl sulfate | 2.0 | |
| Flavor (spearmint type) | 1.0 | |
| Water | 32.9 | |
| | 100.0% | |

A plastics tube was filled with the above composition.

EXAMPLE 4

| | % by weight |
|---|---|
| Alumina trihydrate ($Al_2O_3 \cdot 3H_2O$, gibbsite, average particle size 9μ) | 55 |
| Propylene glycol | 2 ⎫ |
| Sorbitol | 14 ⎬ (4.6 moles/l) |
| Sodium alginate | 0.5 |
| Carrageenan | 0.5 |
| Gelatin | 0.5 |
| Sodium saccharin | 0.1 |
| Sodium monofluorophosphate | 0.76 |
| Lauroyl diethanol amide | 1.5 |
| Sodium lauryl sulfate | 1.5 |
| Flavor | 1.0 |
| Water | 22.64 |
| | 100.0% |

A laminate tube formed of an aluminum foil having a plastics coating on each surface was filled with the above composition. The flavor used in the above composition was a mixture of the following components:

| | | |
|---|---|---|
| l-menthol | 0.3 | parts by weight |
| carvone | 0.05 | parts by weight |
| anethole | 0.1 | parts by weight |
| peppermint oil | 0.5 | parts by weight |
| spearmint oil | 0.05 | parts by weight |

EXAMPLE 5

| | % by weight | |
|---|---|---|
| Alumina hydrate (Al$_2$O$_3$.H$_2$O, boehmite, average particle size 20μ) | 50.0 | |
| Propylene glycol | 3.0 | |
| Glycerine | 12.0 | (7.3 moles/l) |
| Sorbitol | 5.0 | |
| Sodium carboxymethyl cellulose (average degree of etherification 0.8) | 1.0 | |
| Carrageenan | 0.2 | |
| Sodium saccharin | 0.1 | |
| Sodium lauryl sulfate | 1.0 | |
| Flavor (double mint type) | 0.8 | |
| Water | 26.9 | |
| | 100.0% | |

A plastics tube was filled with the above composition.

EXAMPLE 6

| | % by weight | |
|---|---|---|
| Alpha-alumina (average particle size 3μ) | 15 | |
| Glycerine | 50 | |
| Sorbitol | 10 | (28.6 moles/l) |
| Sodium carboxymethyl cellulose (average degree of etherification 0.88) | 1.0 | |
| Sodium saccharin | 0.1 | |
| Sodium lauryl sulfate | 2.0 | |
| Flavor (peppermint type) | 1.0 | |
| Water | 20.9 | |
| | 100.0% | |

A plastics tube was filled with the above composition.

EXAMPLE 7

| | % by weight | |
|---|---|---|
| Alpha-alumina | 56 | |
| Propylene glycol | 2 | |
| Sorbitol | 16 | (5.3 moles/l) |
| Sodium carboxymethyl cellulose | 1.0 | |
| Sodium saccharin | 0.1 | |
| Sodium fluoride | 0.22 | |
| Sodium lauryl sulfate | 2.0 | |
| Flavor (spearmint type) | 1.0 | |
| Water | 21.68 | |
| | 100.0% | |

A laminate tube formed of an aluminum foil having a plastics coating on each surface was filled with the above composition.

EXAMPLE 8

| | % by weight | |
|---|---|---|
| Alumina hydrate (Al$_2$O$_3$.H$_2$O, boehmite, average particle size 20μ) | 50 | |
| Propylene glycol | 3 | |
| Glycerine | 12 | (7.5 moles/l) |
| Sorbitol | 5 | |
| Stannous fluroide | 0.41 | |
| Sodium carboxymethyl cellulose | 1.5 | |
| Sodium saccharin | 0.1 | |
| Sodium lauryl sulfate | 1.0 | |
| Flavor (spearmint type) | 0.5 | |
| Water | 26.49 | |

| | % by weight |
|---|---|
| | 100.0% |

A laminate tube formed of an aluminum foil having a plastics coating on each surface was filled with the above composition.

What is claimed is:

1. A toothpaste composition with which a plastics container is filled, characterized in that the toothpaste composition comprises an aluminum oxide compound as a main abrasive, water, a polyhydric alcohol in an amount of 5.0 to 100 moles per liter of water in the toothpaste composition and an alkali metal salt of carboxymethyl cellulose having an average degree of etherification of 0.75 to 0.90 in an amount of 0.2 to 5% by weight of the total weight of the toothpaste composition.

2. A toothpaste composition according to claim 1 wherein the aluminum oxide compound is present in an amount of 10 to 70% by weight of the total weight of the composition.

3. A toothpaste composition according to claim 1 wherein the aluminum oxide compound has the fomula:

$$Al_2O_3.nH_2O$$

wherein n has a value ranging from 0 to 3.

4. A toothpaste composition according to claim 3 wherein the aluminum oxide compound is aluminum oxide trihydrate.

5. A toothpaste composition according to claim 1 wherein the polyhydric alcohol is present in an amount of 5.0 to 15 moles per liter of water in the toothpaste composition.

6. A toothpaste composition according to claim 1 wherein the polyhydric alcohol is selected from the group consisting of ethylene glycol, propylene glycol, 1,3-butylene glycol, polyethylene glycol, glycerine, xylitol, maltitol, lactitol and sorbitol, and mixtures thereof.

7. A toothpaste composition according to claim 1 wherein the plastics container is selected from the group consisting of a plastic tube formed solely of plastics material, a laminate tube comprising an aluminum foil coated with a plastics layer on an inner or each surface and formed into a tube, and a plastic bottle.

8. A toothpaste composition according to claim 1 wherein the pH of the toothpaste composition is 4.5 to 10.

9. A toothpaste composition with which a plastics container is filled, characterized in that the toothpaste composition comprises an aluminum oxide compound as a main abrasive, water, a polyhydric alcohol in an amount of 4.0 to 100 moles per liter of water in the toothpaste composition, a fluoride and an alkali metal salt of carboxymethyl cellulose having an average degree of etherification of 0.75 to 0.90 in an amount of 0.2 to 5% by weight of the total weight of the toothpaste composition.

10. A toothpaste composition according to claim 9 wherein the fluoride is an alkali metal monofluoro phosphate.

11. A toothpaste composition according to claim 10 wherein the alkali metal monofluorophosphate is present in an amount of 0.1 to 1% by weight of the total weight of the composition.

12. A toothpaste composition according to claim 9 wherein the aluminum oxide compound is present in an amount of 10 to 70% by weight of the total weight of the composition.

13. A toothpaste composition according to claim 9 wherein the aluminum oxide compound has the formula:

$$Al_2O_3 \cdot nH_2O$$

wherein n has a value ranging from 1 to 3.

14. A toothpaste composition according to claim 13 wherein the aluminum oxide compound is aluminum oxide trihydrate.

15. A toothpaste composition according to claim 9 wherein the polyhydric alcohol is present in an amount of 4.0 to 15 moles per liter of water in the toothpaste composition.

16. A toothpaste composition according to claim 9 wherein the polyhydric alcohol is selected from the group consisting of ethylene glycol, propylene glycol, 1,3-butylene glycol, polyethylene glycol, glycerine, xylitol, maltitol, lactitol and sorbitol, and mixtures thereof.

17. A toothpaste composition according to claim 9 wherein the plastics container is selected from the group consisting of a plastic tube formed solely of plastics material, a laminate tube comprising an aluminum foil coated with a plastics layer on an inner or each surface and formed into a tube, and a plastic bottle.

18. A toothpaste composition according to claim 9 wherein the pH of the toothpaste composition is 4.5 to 10.

19. A toothpaste composition comprising: an aluminium oxide compound as a main abrasive, water, a polyhydric alcohol in an amount of 4.0 to 100 moles per liter of water in the toothpaste composition, a fluoride and an alkali metal salt of carboxymethyl cellulose having an average degree of etherification of 0.75 to 0.90 in an amount of 0.2 to 5% by weight of the total weight of the toothpaste composition wherein said toothpaste compositon exhibits antiseptic action against aerobic bacteria.

20. A toothpaste container filled with a toothpaste composition, comprising: a toothpaste container having a plastic layer on the inner surface thereof and a toothpaste composition packaged in said container, said toothpaste composition comprising an aluminum oxide compound as a main abrasive, water, a polyhydric alcohol in an amount of 4.0 to 100 moles per liter of water in the toothpaste composition, a fluoride and an alkali metal salt of carboxymethyl cellulose having an average degree of etherification of 0.75 to 0.90 in an amount of 0.2 to 5% by weight of the total weight of the toothpaste composition wherein said toothpaste composition exhibits antiseptic action against aerobic bacteria when stored in said container.

21. A toothpaste container filled with a toothpaste composition according to claim 20, wherein said container is capable of restoring its shape after pressure is applied thereto to squeeze a desired amount of toothpaste out of said container.

* * * * *